US008623348B2

(12) United States Patent
Lee et al.

(10) Patent No.: US 8,623,348 B2
(45) Date of Patent: Jan. 7, 2014

(54) INTERFERON-α (IFN-α) FUSED PROTEINS COMPRISING IFN-α AND A CYTOPLASMIC TRANSDUCTION PEPTIDE (CTP)

(75) Inventors: Chan Kyu Lee, Seoul (KR); Seonyoung Yang, Incheon (KR); Eun Ju Kang, Yongin-si (KR); Kang Ryu, Incheon (KR); Hyun Soo Lee, Seoul (KR); Yong Soo Bae, Suwon-si (KR)

(73) Assignee: JW Pharmaceutical Corporation, Seoul (KR)

( * ) Notice: Subject to any disclaimer, the term of this patent is extended or adjusted under 35 U.S.C. 154(b) by 32 days.

(21) Appl. No.: 13/260,490

(22) PCT Filed: Mar. 27, 2009

(86) PCT No.: PCT/KR2009/001575
§ 371 (c)(1),
(2), (4) Date: Feb. 21, 2012

(87) PCT Pub. No.: WO2010/110503
PCT Pub. Date: Sep. 30, 2010

(65) Prior Publication Data

US 2012/0134961 A1 May 31, 2012

(51) Int. Cl.

| | |
|---|---|
| ***A61K 38/21*** | (2006.01) |
| ***A61K 39/00*** | (2006.01) |
| ***A61K 39/385*** | (2006.01) |
| ***C07K 14/56*** | (2006.01) |
| ***C12P 21/04*** | (2006.01) |

(52) U.S. Cl.
USPC .................... 424/85.7; 424/185.1; 424/192.1; 530/351; 435/69.51; 435/70.1

(58) Field of Classification Search
None
See application file for complete search history.

(56) References Cited

U.S. PATENT DOCUMENTS

| | | | | |
|---|---|---|---|---|
| 6,177,074 | B1 * | 1/2001 | Glue et al. | 424/85.7 |
| 6,319,691 | B1 * | 11/2001 | Pang | 435/69.7 |
| 2005/0019306 | A1 | 1/2005 | Horvath et al. | |
| 2005/0154188 | A1 * | 7/2005 | Kim et al. | 530/329 |
| 2009/0098049 | A1 * | 4/2009 | Dowdy et al. | 424/9.1 |

FOREIGN PATENT DOCUMENTS

WO WO 2009/019456 A1 2/2009

OTHER PUBLICATIONS

Kim et al., "Cytoplasmic Transduction Peptide (CTP): New Approach for the Delivery of Biomolecules into Cytoplasm in vitro and in vivo," Exp. Cell Res. 312:1277-1288, 2006.

* cited by examiner

*Primary Examiner* — Robert Landsman
*Assistant Examiner* — Bruce D Hissong
(74) *Attorney, Agent, or Firm* — Clark & Elbing LLP

(57) ABSTRACT

Disclosed is an interferon-α (IFN-α) fused protein having IFN-α fused to a cytoplasmic transduction peptide (CTP). The disclosure relates to a fused protein wherein a CTP, which binds well to cell-membrane barriers and enables translocation into the liver, is genetically fused to a human IFN-α, thereby enhancing the conjugation capacity of cell membranes and antiviral activity, inhibiting CTP transport into the cell nucleus, and enhancing the translocation and settlement of the fused protein into the liver and of transduction to the liver tissue. Accordingly, it is possible to develop protein-based medicines effective for preventing or treating various liver diseases associated with viral infection at low doses.

23 Claims, 10 Drawing Sheets

Figure 1

A human interferon-α gene synthesized by PCR (sIFN) in consideration of the codon usage in E. coli.

```
TCTAGAAAAA ACCAAGGAGG TAATAACATA TGTGCGATCT GCCGCAGACC CATAGCCTGG   60
GCAGCCGTCG TACCCTGATG CTGCTGGCGC AGATGCGTCG TATCAGCCTG TTTAGCTGCC  120
TGAAAGATCG TCATGATTTT GGCTTTCCGC AGGAAGAATT TGGCAACCAG TTTCAGAAAG  180
CGGAAACCAT CCCGGTGCTG CATGAAATGA TCCAGCAGAT CTTTAACCTG TTTAGCACCA  240
AAGATAGCAG CGCGGCGTGG GATGAAACCC TGCTGGATAA ATTTTATACC GAACTGTATC  300
AGCAGCTGAA CGATCTGGAA GCGTGCGTGA TCCAGGGCGT GGGCGTGACC GAAACCCCGC  360
TGATGAAAGA AGATAGCATC CTGGCGGTGC GTAAATATTT TCAGCGTATC ACCCTGTATC  420
TGAAAGAAAA AAAATATAGC CCGTGCGCGT GGGAAGTGGT GCGTGCGGAA ATCATGCGTA  480
GCTTTAGCCT GAGCACCAAC CTGCAAGAAA GCCTGCGTAG CAAAGAATAA TAGCTCGAGG  540
GATCC
```

Figure 2

A gene of human IFN-α (interferon-α) fusion protein synthesized by PCR (sIFN) wherein CTP is fused at the N-terminal of IFN-α

```
TCTAGAAAAA ACCAAGGAGG TAATAACATA TGTATGGTCG TCGTGCACGT CGTCGTCGTC   60
GTCGTTGCGA TCTGCCGCAG ACCCATAGCC TGGGCAGCCG TCGTACCCTG ATGCTGCTGG  120
CGCAGATGCG TCGTATCAGC CTGTTTAGCT GCCTGAAAGA TCGTCATGAT TTTGGCTTTC  180
CGCAGGAAGA ATTTGGCAAC CAGTTTCAGA AAGCGGAAAC CATCCCGGTG CTGCATGAAA  240
TGATCCAGCA GATCTTTAAC CTGTTTAGCA CCAAAGATAG CAGCGCGGCG TGGGATGAAA  300
CCCTGCTGGA TAAATTTTAT ACCGAACTGT ATCAGCAGCT GAACGATCTG GAAGCGTGCG  360
TGATCCAGGG CGTGGGCGTG ACCGAAACCC CGCTGATGAA AGAAGATAGC ATCCTGGCGG  420
TGCGTAAATA TTTTCAGCGT ATCACCCTGT ATCTGAAgGA AAAAAAATAT AGCCCGTGCG  480
CGTGGGAAGT GGTGCGTGCG GAAATCATGC GTAGCTTTAG CCTGAGCACC AACCTGCAAG  540
AAAGCCTGCG TAGCAAAGAA TAATAGCTCG AGGGATCC
```

(*) The portion indicated by underline is the sequence of CTP. Lower cases represent the error produced in PCR amplification, which do not change the original amino acids of the sequence.

An amino acid sequence of human IFN-α (interferon-α) wherein CTP is fused at the N-terminal of IFN-α

```
MYGRRARRRR RRCDLPQTHS LGSRRTLMLL AQMRRISLFS CLKDRHDFGF PQEEFGNQFQ   60
KAETIPVLHE MIQQIFNLFS TKDSSAAWDE TLLDKFYTEL YQQLNDLEAC VIQGVGVTET  120
PLMKEDSILA VRKYFQRITL YLKEKKYSPC AWEVVRAEIM RSFSLSTNLQ ESLRSKE* 177
```

(*) The portion indicated by underline is the sequence of CTP.

Figure 3

A gene of human IFN-α (interferon-α) fusion protein synthesized by PCR (sIFN) wherein a CTP is fused at the C-terminal of IFN-α

```
TCTAGAAAAA ACCAAGGAGG TAATAAaCATA TGTGCGATCT GCCGCAGACC CATAGCCTGG   60
GCAGCCGTCG TACCCTGATG CTGCTGGCGC AGATGCGTCG TATCAGCCTG TTTAGCTGCC  120
TGAAAGATCG TCATGATTTT GGCTTTCCGC AGGAAGAATT TGGCAACCAG TTTCAGAAAG  180
CGGAAACCAT CCCGGTGCTG CATGAAATGA TCCAGCAGAT CTTTAACCTG TTTAGCACCA  240
AAGATAGCAG CGCGGCGTGG GATGAAACCC TGCTGGATAA ATTTTATACC GAACTGTATC  300
AGCAGCTGAA CGATCTGGAA GCGTGCGTGA TCCAGGGCGT GGGCGTGACC GAAACCCCGC  360
TGATGAAAGA AGATAGCATC CTGGCGGTGC GTAAATATTT TCAGCGTATC ACCCTGTATC  420
TGAAAGAAAA AAAATATAGC CCGTGCGCGT GGGAAGTGGT GCGTGCGGAA ATCATGCGTA  480
GCTTTAGCCT GAGCACCAAC CTGCAAGAAA GCCTGCGTAG CAAAGAATAT GGTCGTCGTG  540
CACGTCGTCG TCGTCGTCGT TAATAGCTCG AGGGATCC
```

(*) The portion indicated by underline is the sequence of CTP. Lower cases represent the error produced in PCR amplification, which do not change the original amino acids of the sequence.

An amino acid sequence of human IFN-α (interferon-α) wherein CTP is fused at the C-terminal of IFN-α.

```
MCDLPQTHSL GSRRTLMLLA QMRRISLFSC LKDRHDFGFP QEEFGNQFQK AETIPVLHEM   60
IQQIFNLFST KDSSAAWDET LLDKFYTELY QQLNDLEACV IQGVGVTETP LMKEDSILAV  120
RKYFQRITLY LKEKKYSPCA WEVVRAEIMR SFSLSTNLQE SLRSKEYGRR ARRRRR* 177
```

(*) The portion indicated by underline is the sequence of CTP.

Figure 4

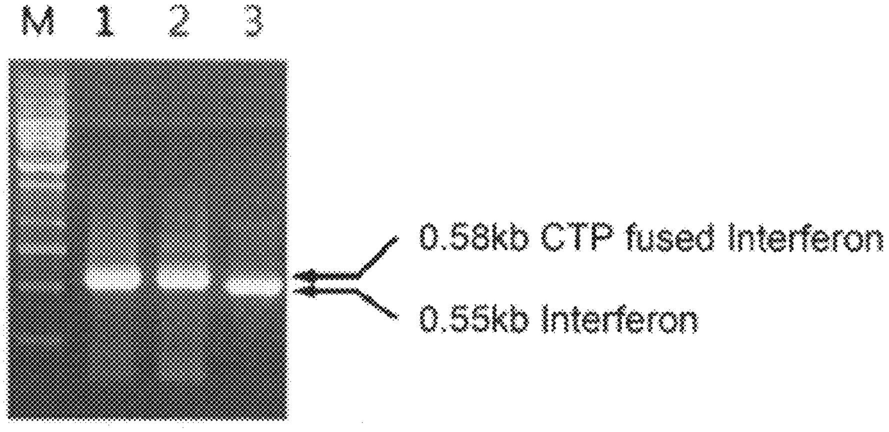

PEG-Interferon PEG-CTP fused Interferon

INTERFERON-α (IFN-α) FUSED PROTEINS COMPRISING IFN-α AND A CYTOPLASMIC TRANSDUCTION PEPTIDE (CTP)

CROSS-REFERENCE TO RELATED APPLICATIONS

This application is the U.S. national stage filing under 35 U.S.C. § 371 of international application PCT/KR2009/001575, filed Mar. 27, 2009.

TECHNICAL FIELD

The present disclosure relates to an interferon-α (IFN-α) fused protein having IFN-α fused to a cytoplasmic transduction peptide (CTP). More particularly, the disclosure relates to a fused protein wherein a CTP, which binds well to cell-membrane barriers and enables translocation into the liver, is fused to a human IFN-α at the N-terminal or C-terminal thereof, thereby enhancing the conjugation capacity of cell membranes, inhibiting CTP transport into the cell nucleus after being introduced into the cell, and enhancing the translocation and settlement of the fused protein into the liver and of transduction to the liver tissue.

BACKGROUND ART

Interferons (IFNs) are used to treat hepatitis and marketed as interferon-α (Intron A: Schering, Roferon A: Roche) or PEGylated IFN (PegIntron: Schering, Pegasys: Roche) wherein PEG is added to make the interferon last longer in the body.

The early side effect of interferon-α therapy includes fever, chills, lethargy, lack of appetite, nausea and myalgia, which occur in most patients in a dose-dependent manner. They are the most severe in the early stage of treatment and usually disappear when the treatment is stopped. Also, it is known that the occurrence and severity of side effects during treatment of chronic hepatitis B patients with PEG-interferon-α are comparable to those in treatment with interferon-α (1).

Due to the dose-dependent side effects associated with the interferon therapy, there is a need of reducing its administration dose.

Throughout the specification, a number of publications and patent documents are referred to and cited. The disclosure of the cited publications and patent documents is incorporated herein by reference in its entirety to more clearly describe the state of the related art and the present disclosure.

DISCLOSURE

The inventors of the present disclosure have made efforts to develop an interferon with improved translocation and settlement into the liver tissue as well as better effect. As a result, they have prepared a fused protein wherein a cytoplasmic transduction peptide (CTP) is fused to a human interferon (IFN) and confirmed that it has improved translocation, penetration and settlement ability into the liver and thus can solve the side effect and cost problems of the existing therapy.

The present disclosure is directed to providing an IFN-α fused protein.

The present disclosure is also directed to providing a nucleotide molecule coding for the IFN-α fused protein.

The present disclosure is also directed to providing a vector including the nucleotide molecule.

The present disclosure is also directed to providing a transformant including the vector.

The present disclosure is also directed to providing method for preparing an IFN-α fused protein.

The present disclosure is also directed to providing a method for purifying an IFN-α fused protein.

The present disclosure is also directed to providing a pharmaceutical composition for preventing or treating a liver disease.

The present disclosure is also directed to providing a method for preventing or treating a liver disease.

Other features and aspects will be apparent from the following detailed description, drawings, and claims.

In an aspect, the present disclosure provides an IFN-α fused protein comprising IFN-α fused to a CTP.

The inventors of the present disclosure have made efforts to develop an interferon with improved translocation and settlement into the liver tissue as well as better effect. As a result, they have prepared a fused protein wherein a CTP is fused to a human IFN and confirmed that it has improved translocation, penetration and settlement ability into the liver and thus can solve the side effect and cost problems of the existing therapy.

As used herein, the term “IFN-α fused protein” refers to a protein comprising IFN-α fused to a CTP.

The CTP included in the IFN-α fused protein of the present disclosure is a delivery peptide developed for the first time by the inventors of the present disclosure to solve the problems of PTD and was patented in several countries (Korean Patent No. 0608558, U.S. Pat. No. 7,101,844 and Japanese Patent No. 4188909). The disclosure of the patents about the CTP is incorporated herein by reference.

The term “cytoplasmic transduction peptide (CTP)” was first coined by the inventors of the present disclosure and refers to a peptide capable of penetrating the cell membranes and settling in the cytoplasm with limited transport into the nucleus.

The CTP included in the IFN-α fused protein of the present disclosure may have a peptide length generally employed in the related art. It may comprise specifically 9-20 amino acids, more specifically 9-15 amino acids, most specifically 11 amino acids.

In a specific embodiment of the present disclosure, the CTP included in the IFN-α fused protein of the present disclosure comprises an amino acid sequence selected from a group consisting of SEQ ID NOS: 13-26. More specifically, it comprises an amino acid sequence selected from a group consisting of SEQ ID NOS: 13-18, 20-22, 25 and 26. Most specifically, it comprises an amino acid sequence selected from a group consisting of SEQ ID NOS: 13 and 25.

The CTP binds well to cell membranes and its transport into the nucleus is inhibited after it is introduced into the cell. Further, since it has less cytotoxicity than other transporters (especially, PTD or polyarginine) and is capable of translocating the fused protein into the liver, it makes a very effective drug delivery peptide for treating liver diseases.

As used herein, the term “interferon-α (IFN-α)” refers to a highly homologous, species-specific protein group of interferon that inhibits viral replication and cell proliferation and regulates immune response.

The IFN-α included in the IFN-α fused protein of the present disclosure is recombinant IFN-α2b, recombinant IFN-α2a, recombinant IFN-α2c, IFN-α-n1 which is a purified mixture of natural α-interferon, consensus α-interferon (see U.S. Pat. Nos. 4,897,471 and 4,695,623) or IFN-α-n3 which is a mixture of natural α-interferon. More specifically, it is IFN-α2a or IFN-α2b. Most specifically, it is IFN-α2b. The method for preparing IFN-α2b is described in detail in U.S. Pat. No. 4,530,901.

In a specific embodiment of the present disclosure, the IFN-α included in the IFN-α fused protein of the present disclosure comprises an amino acid sequence of SEQ ID NO: 28.

In another specific embodiment of the present disclosure, the IFN-α fused protein of the present disclosure has the CTP fused at the N-terminal or C-terminal of the IFN-α. More specifically, the CTP is fused at the N-terminal of the IFN-α.

In a specific embodiment of the present disclosure, when the CTP is fused at the N-terminal of the IFN-α, the IFN-α fused protein of the present disclosure comprises an amino acid sequence of SEQ ID NO: 30.

In another specific embodiment of the present disclosure, when the CTP is fused at the C-terminal of the IFN-α, the IFN-α fused protein of the present disclosure comprises an amino acid sequence of SEQ ID NO: 32.

In another specific embodiment of the present disclosure, the fused protein further comprises polyethylene glycol (PEG) bound thereto. PEGylation for binding the PEG may be performed by methods commonly known in the art (M. J. Roberts, M. D. Bentley et al., Chemistry for peptide and protein PEGylation, *Advanced Drug Delivery Reviews;* 54: 459-476 (2002); Francesco M., Peptide and protein PEGylation: a review of problems and solutions, *Veronese Biomaterials;* 22: 405-417 (2001)).

In a more specific embodiment of the present disclosure, the PEG bound to the fused protein of the present disclosure has a molecular weight of 10-100 kDa, more specifically 10-60 kDa, and most specifically 15-40 kDa. The PEG having a molecular weight of 10-100 kDa reduces renal clearance and extends residence in blood, thus reducing the administration dose of the fused protein of the present disclosure.

In another aspect, the present disclosure provides a nucleotide molecule coding for the IFN-α fused protein of the present disclosure described above.

As used herein, the term "nucleotide molecule" comprehensively embraces DNA (gDNA and cDNA) and RNA molecules. The nucleotide unit may be either naturally occurring nucleotides or analogues with modification at the sugar or base moieties (Scheit, Nucleotide Analogs, John Wiley, New York (1980); Uhlman and Peyman, *Chemical Reviews,* 90: 543-584 (1990)).

The IFN-α included in the IFN-α fused protein of the present disclosure comprises nucleotides 30-533 of a nucleotide sequence of SEQ ID NO: 27. The nucleotide molecule coding for the IFN-α fused protein of the present disclosure comprises, most specifically, nucleotides 30-566 of a nucleotide sequence of SEQ ID NO: 29 or nucleotides 31-567 of a nucleotide sequence of SEQ ID NO: 31. It is to be understood that the nucleotide molecule of the present disclosure coding for the CTP-fused IFN-α also includes a nucleotide sequence having a substantial identity to the nucleotide sequence described above. The substantial identity means that, when a nucleotide sequence is aligned to maximally match the nucleotide sequence of the present disclosure and the alignment is analyzed using an algorithm commonly used in the art, it has an identity of at least 80%, more specifically at least 90%, and most specifically at least 95%.

In another aspect, the present disclosure provides a vector for expressing an IFN-α fused protein, comprising the nucleotide molecule of the present disclosure coding for the CTP-fused IFN-α.

The vector system of the present disclosure can be established according to various methods known in the art. Details can be found in Sambrook et al., Molecular Cloning, A Laboratory Manual, Cold Spring Harbor Laboratory Press (2001), which is incorporated herein by reference.

Typically, the vector of the present disclosure may be established as a cloning vector or an expression vector. And, the vector of the present disclosure may be established using a prokaryotic or eukaryotic cell as host. Specifically, a prokaryotic cell may be used as the host considering that the nucleotide sequence of the present disclosure is derived from a prokaryotic cell and culturing is more convenient.

When the vector of the present disclosure is an expression vector and a prokaryotic cell is a host, a powerful promoter for transcription (e.g., tac promoter, lac promoter, lacUV5 promoter, lpp promoter, $p_L^{\lambda}$ promoter, $p_R^{\lambda}$ promoter, rac5 promoter, amp promoter, recA promoter, SP6 promoter, trp promoter, T7 promoter, etc.), a ribosome binding site for initiation of translation, and a transcription/translation termination sequence are included in general. When *E. coli* is used as the host cell, the promoter and operator regions involved in tryptophan biosynthesis in *E. coli* (Yanofsky, C., *J. Bacteria,* 158: 1018-1024 (1984)) and the left side promoter of phage λ ($p_L^{\lambda}$ promoter, Herskowitz, I. and Hagen, D., *Ann. Rev. Genet.,* 14: 399-445 (1980)) can be used as a regulatory site.

Meanwhile, the vector that can be used in the present disclosure can be constructed by using a plasmid (e.g., pSC101, ColE1, pBR322, pUC8/9, pHC79, pUC19, pET, etc.), a phage (e.g., λgt4.λB, λ-Charon, λΔz1, M13, etc.) or a virus (e.g., SV40, etc.) that are typically used in the art.

When the vector of the present disclosure is an expression vector and has an eukaryotic cell as a host, a promoter originating from mammalian genome (e.g., metallothionein promoter) or promoter originating from mammalian virus (e.g., adenovirus late promoter, vaccinia virus 7.5K promoter, SV40 promoter, cytomegalovirus promoter and tk promoter of HSV) can be used. As a transcription termination sequence, polyadenylation sequence is generally used.

The vector of the present disclosure may be fused with other sequence, if necessary, for easier purification of the IFN-α fused protein of the present disclosure expressed thereby. The fused sequence may be, for example, glutathione S-transferase (Pharmacia, USA), maltose-binding protein (NEB, USA), FLAG (IBI, USA), hexahistidine (6×His; Qiagen, USA), or the like, but is not limited thereto.

In a specific embodiment of the present disclosure, the IFN-α fused protein expressed by the vector of the present disclosure is purified by cation exchange chromatography and gel filtration chromatography.

Meanwhile, the expression vector of the present disclosure may comprise an antibiotic-resistant gene typically used in the art as a selection marker. Examples thereof include but are not limited to genes resistant to ampicillin, gentamycin, carbenicillin, chloramphenicol, streptomycin, kanamycin, geneticin, neomycin and tetracycline.

In another aspect, the present disclosure provides a transformant comprising the vector of the present disclosure described above.

With respect to a host cell, any one known in the art to be capable of stably and continuously cloning and expressing the vector of the present disclosure can be used. Examples thereof include *Bacillus* sp. strains including *E. coli* JM109, *E. coli* BL21(DE3), *E. coli* RR1, *E. coli* LE392, *E. coli* B, *E. coli* X 1776, *E. coli* W3110, *Bacillus subtilis, Bacillus thuringiensis*, etc., and intestinal bacteria and strains including *Salmonella typhimurium, Serratia marcescens* and various *Pseudomonas* sp.

In addition, when a eukaryotic cell is transformed with the vector of the present disclosure, yeast (*Saccharomyces cerevisiae*), an insect cell or a human cell (e.g., CHO (Chinese hamster ovary) cell line, W138, BHK, COS-7, 293, HepG2, 3T3, RIN and MDCK cell line) can be used as a host cell.

When the host cell is a prokaryotic cell, delivery of the vector of the present disclosure into the host cell can be carried out by the $CaCl_2$ method (Cohen, S. N. et al., *Proc. Natl. Acac. Sci. USA,* 9: 2110-2114 (1973)), the Hannahan's method (Cohen, S. N. et al., *Proc. Natl. Acac. Sci. USA,* 9: 2110-2114 (1973); Hanahan, D., *J. Mol. Biol.,* 166: 557-580 (1983)), the electroporation method (Dower, W. J. et al., *Nucleic. Acids Res.,* 16: 6127-6145 (1988)), and the like. And, when the host cell is an eukaryotic cell, the vector can be introduced to the host cell via the microinjection method (Capecchi, M. R., *Cell,* 22: 479 (1980)), the calcium phosphate precipitation method (Graham, F. L. et al., *Virology,* 52: 456 (1973)), the electroporation method (Neumann, E. et al., *EMBO J.,* 1: 841 (1982)), the liposome-mediated transfection method (Wong, T. K. et al., *Gene,* 10: 87 (1980)), the DEAE-dextran treatment method (Gopal, *Mol. Cell. Biol.,* 5: 1188-1190 (1985)), the gene bombardment method (Yang et al., *Proc. Natl. Acad. Sci.,* 87: 9568-9572 (1990)), and the like.

The vector introduced into the host cell may be expressed there. In this case, a large amount of the IFN-α fused protein of the present disclosure can be produced. For example, when the expression vector comprises the lac promoter, the host cell may be treated with IPTG to induce gene expression.

Hereinafter, the methods for preparing and purifying the IFN-α fused protein of the present disclosure will be described. In the following description, the matters that have been already described above will not be described again in order to avoid unnecessary redundancy and complexity.

In another aspect, the present disclosure provides a method for preparing an IFN-α fused protein, comprising the steps of: (a) preparing an expression vector comprising the nucleotide molecule coding for the IFN-α fused protein of the present disclosure described above, which is operably linked to a promoter; (b) culturing a transformant transformed with the expression vector of the step (a); and (c) obtaining the IFN-α fused protein from the transformant cultured in the step (b).

As used herein, the term "operably linked" refers to a functional linkage between a nucleotide expression control sequence (e.g., promoter, signal sequence or array of transcription factor binding sites) and another nucleotide sequence, wherein the expression control sequence directs the transcription and/or translation of the another nucleotide sequence.

In another aspect, the present disclosure provides a method for purifying an IFN-α fused protein, comprising the steps of: (a) culturing a transformant transformed with an expression vector comprising the nucleotide molecule coding for the IFN-α fused protein of the present disclosure described above, which is operably linked to a promoter; (b) obtaining an inclusion body of the IFN-α fused protein from the transformant cultured in the step (a); and (c) lysing the inclusion body of the step (b) in a solubilization buffer of pH 10-12 and stirring the resultant at 4-25° C. and pH 8-10 in a refolding buffer.

In a specific embodiment of the present disclosure, the solubilization buffer comprises tris-HCl, EDTA and urea, and the refolding buffer is selected from a group consisting of tris-HCl, EDTA, urea, sucrose, and oxidized or reduced glutathione.

In another aspect, the present disclosure provides a pharmaceutical composition for preventing or treating a liver disease comprising: (a) a pharmaceutically effective amount of the IFN-α fused protein of the present disclosure described above; and (b) a pharmaceutically acceptable carrier.

In another aspect, the present disclosure provides a method for preventing or treating a liver disease, comprising administering a pharmaceutical composition comprising: (a) a pharmaceutically effective amount of the IFN-α fused protein of the present disclosure described above; and (b) a pharmaceutically acceptable carrier to a subject.

In another aspect, the present disclosure provides a use of the IFN-α fused protein of the present disclosure described above for preparing a pharmaceutical composition for preventing or treating a liver disease.

In a specific embodiment of the present disclosure, the composition of the present disclosure is administered intravascularly. More specifically, the active ingredient of the intravascularly administered composition is a PEGylated fused protein wherein the CTP is fused to the IFN-α.

The liver disease prevented or treated by the composition of the present disclosure includes liver cancer, hepatitis, liver cirrhosis and other liver diseases. Specifically, it includes liver cancer and hepatitis. More specifically, it is hepatitis B or C.

In another aspect, the present disclosure provides a CTP-drug fused protein wherein the CTP of the present disclosure described above is fused to a drug for treating a liver disease.

In addition, the present disclosure provides a pharmaceutical composition for preventing or treating a liver disease, comprising: (a) a pharmaceutically effective amount of a CTP-drug fused protein wherein the CTP is fused to a drug for treating a liver disease; and (b) a pharmaceutically acceptable carrier.

In another aspect, the present disclosure provides a method for preventing or treating a liver disease, comprising: administering a pharmaceutical composition comprising: (a) a pharmaceutically effective amount of a CTP-drug fused protein wherein the CTP is fused to a drug for treating a liver disease; and (b) a pharmaceutically acceptable carrier to a subject.

In another aspect, the present disclosure provides a use of a CTP-drug fused protein wherein the CTP is fused to a drug for treating a liver disease for preparing a pharmaceutical composition for preventing or treating a liver disease.

In a specific embodiment of the present disclosure, the drug for treating a liver disease includes various drugs known in the art. Specifically, it may be a parenterally administered drug. More specifically, it may be an intravascularly administered drug.

The fusion of the drug for treating a liver disease with the CTP may be carried out according to the method for preparing the IFN-α fused protein of the present disclosure or protein fusion techniques known in the art, depending on the kind and type of the drug. For example, it may be accomplished using a peptide linker, but without being limited thereto.

As used herein, the term "pharmaceutically effective amount" refers to an amount sufficient to achieve the effect or activity of the fused protein of the present disclosure.

The pharmaceutical composition of the present disclosure may be prepared into a unit dosage form along with a pharmaceutically acceptable, nontoxic carrier, adjuvant or excipient, and may be administered orally, parenterally, by inhalation spray, rectally or topically. Specifically, it may be administered parenterally. For topical administration, transdermal patches or iontophoresis devices may be used.

As used herein, the term "parenteral administration" includes subcutaneous injection, intravenous injection, intramuscular injection, and intrasternal injection or infusion. Details about the pharmaceutical formulations can be found, for example, in Hoover, John E., Remington's Pharmaceutical Sciences, Mack Publishing Co., Easton, Pa. 1975 and also in Liberman, H. A. and Lachman, L., Eds., Pharmaceutical Dosage Forms, Marcel Decker, New York, N.Y., 1980.

The pharmaceutically acceptable carrier included in the pharmaceutical composition of the present disclosure is one commonly used in the art. Examples include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but are not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in Remington's Pharmaceutical Sciences (19th ed., 1995).

An appropriate dosage of the pharmaceutical composition of the present disclosure may be determined variously depending on such factors as preparation method, administration method, age, body weight and sex of the patient, pathological condition, diet, administration time, administration route, excretion rate or response sensitivity. Specifically, the dosage of the pharmaceutical composition of the present disclosure for an adult may be 0.001-100 μg/kg (body weight).

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

DESCRIPTION OF DRAWINGS

FIG. 1 shows a human IFN-α (interferon-α) gene synthesized by PCR (sIFN) in consideration of the codon usage of *E. coli* (SEQ ID NO:27).

FIG. 2 shows a gene synthesized by PCR (sIFN) wherein a cytoplasmic transduction peptide (CTP) is fused at the N-terminal of IFN-α and an amino acid sequence thereof (SEQ ID NOs:29 and 30).

FIG. 3 shows a gene synthesized by PCR (sIFN) wherein a CTP is fused at the C-terminal of IFN-α and an amino acid sequence thereof (SEQ ID NOs:31 and 32).

FIG. 4 shows a PCR result of sIFN, CTP-sIFN and sIFN-CTP (lane 1: CTP-sIFN, lane 2: sIFN-CTP, lane 3: sIFN).

MODE FOR INVENTION

Figure 5A:
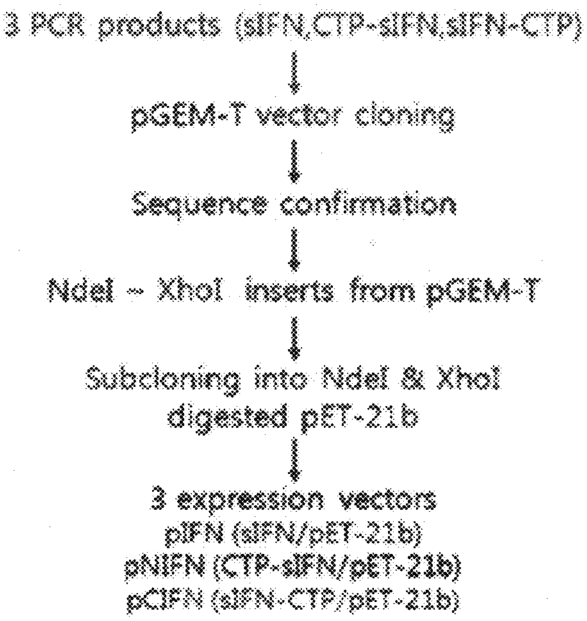
FIG. 5*a* shows a procedure of preparing expression vectors for pIFN, pNIFN and pCIFN.

The examples and experiments will now be described. The following examples and experiments are for illustrative purposes only and it will be apparent to those skilled in the art that the scope of the present disclosure is not limited by the following examples.

EXAMPLE 1

Synthesis of Template of Human Interferon-α (IFN-α) Gene for High-Level Expression in *E. coli*

Since the Interferon-α (IFN-α) gene originating from human contains a considerable amount of codons that are not expressed well in *E. coli*, it is known that the degree of expression of IFN protein is very low in the absence of modification. In particular, such codon clusters as AGG/AGA, CUA, AUA, CCA or CCC are reported to degrade both quantity and quality of the proteins expressed in *E. coli* (2-3).

Among them, the AGG codon cluster has the worst effect, presumably because the available tRNA pool is limited and the cluster binds competitively with ribosomes due to similarity to the Shine-Dalgarno sequence (4-5).

Thus, in order to improve the degree of expression, the inventors chemically synthesized the full sequence of the human IFN-α gene excluding the rare codon, in consideration of the codon usage frequency of *E. coli*. First, in order to obtain the human IFN-α2b gene optimized for the codon usage of *E. coli*, they synthesized the 6 oligomers shown in Table 1 such that the 18 nucleotides overlap with each other:

TABLE 1

| Oligomer name | Oligomer sequence | SEQ ID NO |
|---|---|---|
| sIFN-1 | 5'- TGC GAT CTG CCG CAG ACC CAT AGC CTG GGC AGC CGT CGT ACC CTG ATG CTG CTG GCG CAG ATG CGT CGT ATC AGC CTG TTT AGC TGC CTG AAA GAT CGT -3' | 1 |
| sIFN-2 | 5'- GAT CAT TTC ATG CAG CAC CGG GAT GGT TTC CGC TTT CTG AAA CTG GTT GCC AAA TTC TTC CTG CGG AAA GCC AAA ATC ATG ACG ATC TTT CAG GCA GCT -3' | 2 |

TABLE 1-continued

| Oligomer name | Oligomer sequence | SEQ ID NO |
|---|---|---|
| sIFN-3 | 5'- GTG CTG CAT GAA ATG ATC CAG CAG ATC TTT AAC CTG TTT AGC ACC AAA GAT AGC AGC GCG GCG TGG GAT GAA ACC CTG CTG GAT AAA TTT TAT ACC GAA -3' | 3 |
| sIFN-4 | 5'- ATC TTC TTT CAT CAG CGG GGT TTC GGT CAC GCC CAC GCC CTG GAT CAC GCA CGC TTC CAG ATC GTT CAG CTG CTG ATA CAG TTC GGT ATA AAA TTT ATC -3' | 4 |
| sIFN-5 | 5'- CCG CTG ATG AAA GAA GAT AGC ATC CTG GCG GTG CGT AAA TAT TTT CAG CGT ATC ACC CTG TAT CTG AAA GAA AAA AAA TAT AGC CCG TGC GCG TGG GAA -3' | 5 |
| sIFN-6 | 5'- CTA TTA TTC TTT GCT ACG CAG GCT TTC TTG CAG GTT GGT GCT CAG GCT AAA GCT ACG CAT GAT TTC CGC ACG CAC CAC TTC CCA CGC GCA CGG GCT -3' | 6 |

EXAMPLE 2

Synthesis of IFN or CTP-fused IFN gene by PCR

In order to obtain DNA of IFN or IFN with the CTP peptide fused at the N- or C-terminal, SOEing PCR was carried out using the primers shown in Table 2 and using the human IFN genes described in Table 1 as template (6):

TABLE 2

| Primer name | Primer sequence | SEQ ID NO |
|---|---|---|
| CFN-1 | 5'-TATGGTCGTCGTGCACGTCGTCGTCGTCGTCGTTGCGATCTGCCGCAGACC-3' | 7 |
| CFN-2 | 5'-TAATCTAGAAAAAACCAAGGAGGTAATAACATATGTATGGTCGTCGTGCACGT-3' | 8 |
| CFN-3 | 5'-CAAGGATCCCTCGAGCTATTATTCTTTGCTACGCAGGCT-3' | 9 |
| CFN-4 | 5'-GCCTCTAGAAAAAACCAAGGAGGTAATAACATATGTGCGATCTGCCGCAG-3' | 10 |
| CFN-5 | 5'-ACGACGACGACGTGCACGACGACCATATTCTTTGCTACGCAGGCT-3' | 11 |
| CFN-6 | 5'-TAAGGATCCCTCGAGCTATTAACGACGACGACGACGACGTGCACG-3' | 12 |

EXAMPLE 2-1

Synthesis of IFN-α Gene (sIFN) Modified for High-Level expression of IFN Protein The gene originating from human has the problem in that the level of expression is very low in *E. coli* in the absence of modification. To solve this problem, the inventors carried out two-step reactions to obtain synthetic gene in consideration of the codon usage of *E. coli*. First, they mixed the 6 oligomers shown in Table 1, with the same quantity, and allowed them to react at 60° C. for 30 minutes after adding pfu DNA polymerase and dNTP mixture. As a result, a template of human IFN-α gene was synthesized according to the codon usage. Then, PCR was carried out using the template and using the CFN-4 and CFN-3 primers. As a result, the human IFN-α gene was obtained as shown in FIG. 1 (SEQ ID NO: 27). The obtained ~0.55 kb PCR product is shown as lane 3 in FIG. 4.

EXAMPLE 2-2

Synthesis of N-terminal CTP-Fused IFN-α Gene (CTP-sIFN)

Three-step reactions were carried out to attach the CTP peptide at the N-terminal of IFN-α. First, the 6 oligomers shown in Table 1 were mixed with the same quantity and were allowed to react at 60° C. for 30 minutes after adding pfu DNA polymerase and dNTP mixture. As a result, a template of human IFN-α gene was synthesized according to the codon usage. Then, PCR was carried out using the template and using the CFN-1 and CFN-3 primers, and then using the template and using the CFN-2 and CFN-3 primers. As a result, the human IFN-α gene with the CTP fused at the N-terminal was obtained as shown in FIG. 2 (SEQ ID NO: 29). The obtained ~0.58 kb PCR product is shown as lane 1 in FIG. 4.

EXAMPLE 2-3

Synthesis of C-terminal CTP-Fused IFN-α Gene (sIFN-CTP)

A template of human IFN-α gene was synthesized in the same manner as in Example 2-2. Then, PCR was carried out using the template and using the CFN-4 and CFN-5 primers, and then using the template and using the CFN-4 and CFN-6 primers. As a result, the human IFN-α gene with the CTP fused at the C-terminal was obtained as shown in FIG. 3 (SEQ ID NO: 31). The obtained ~0.58 kb PCR product is shown as lane 2 in FIG. 4.

EXAMPLE 3

Preparation of Vector for Expressing IFN and CTP-Fused IFN in *E. Coli*

Figure 5B:
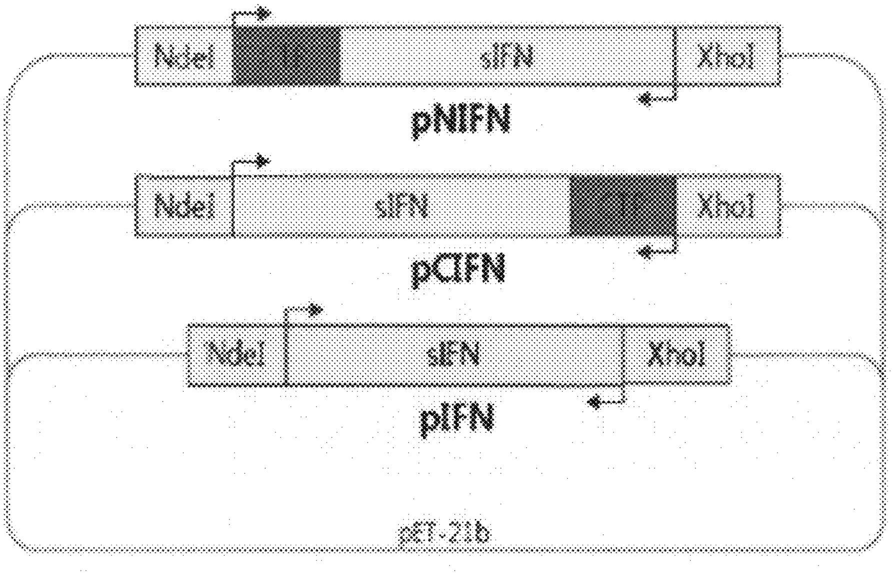
FIG. 5*b* shows gene maps of pET-21b each comprising a nucleotide sequence coding for sIFN, CTP-sIFN and sIFN-CTP proteins.

In order to express the three genes (sIFN, CTP-sIFN and sIFN-CTP) obtained by PCR in *E. coli*, they were cloned respectively to the pET-21b vector (Novagen) as shown in FIG. 5a to obtain three expression vectors pIFN, pNIFN and pCIFN. First, each PCR product was cloned to the pGEM-T vector to obtain the three recombinant pGEM-T vectors (sIFN/pGEM-T, CTP-sIFN/pGEM-T and sIFN-CTP/pGEM-T), without modification of the amino acid sequence. From the recombinant pGEM-T vectors, inserts were obtained using the restriction enzyme sets used for the PCR, which were then introduced to the pET-21b vector to finally obtain the three expression vectors (pIFN, pNIFN and pCIFN) (FIG. 5b).

EXAMPLE 4

Confirmation of Expression of IFN and CTP-Fused IFN in *E. coli*

Figure 6:
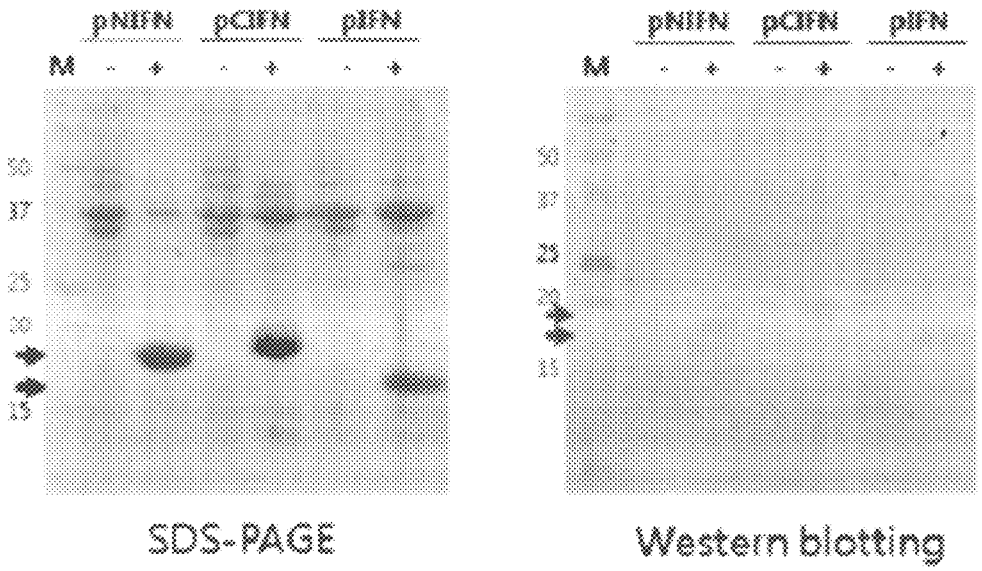
FIG. 6 shows a result of SDS-PAGE and western blotting analysis for IFN and CTP-fused IFN proteins (−: uninduced, +: IPTG-induced).

*E. coli* BL21(DE3) (Novagen) was transformed with the expression vectors constructed from the pET-21b vector (Novagen) to obtain three kinds of bacteria (*E. coli* BL21 (DE3)/pIFN, pNIFN and pCIFN), which were cultured in LB medium until the absorbance at 600 nm was 0.4. Then, after adding 0.4 mM IPTG and culturing further for 4 hours, it was confirmed by SDS-PAGE and western blotting that IFN and CTP-fused IFN were produced (FIG. 6).

EXAMPLE 5

Preparation of IFN and CTP-Fused IFN

IFN and CTP-fused IFN were produced in large scale using a 5-L fermentation tank and then purified.

EXAMPLE 5-1

Large-Scale Production Using 5-L Fermentation Tank

Figure 7:
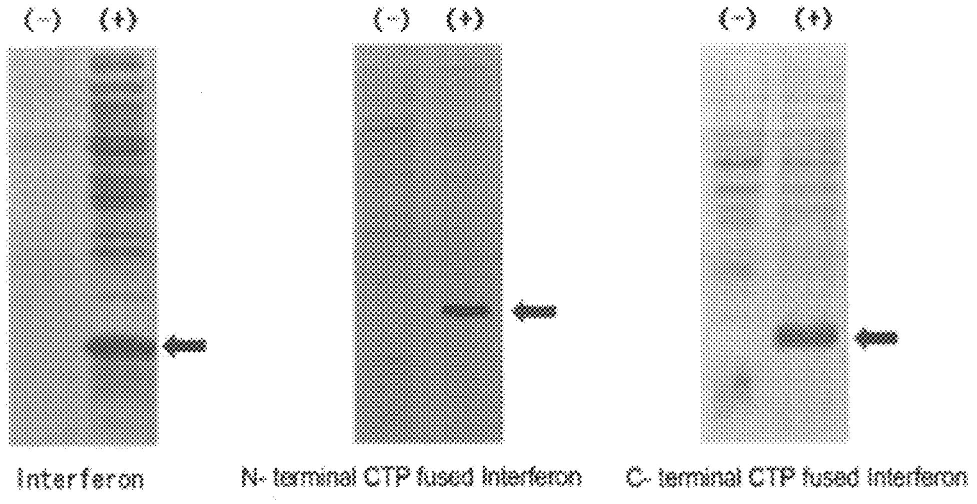
FIG. 7 shows a result of SDS-PAGE analysis for IFN, CTP-IFN and IFN-CTP proteins (−: uninduced, +: IPTG-induced).

To produce interferon (pIFN) or CTP-fused interferon (pNIFN or pCIFN) in large scale using the bacteria *E. coli* BL21(DE3)/pIFN, pNIFN and pCIFN, large-scale culturing was carried out using a 5 L-fermentation tank (Biostat® B, B. Braun Biotech International). First, after adding ampicillin to 60 mL of 2×YT medium (16 g of tryptone, 10 g of yeast extract and 5 g/L NaCl) to 50 μg/mL, and then adding each bacteria, culturing was carried out at 37° C. for 16 hours. The culture was transferred to a 3 L of TB fermentation medium (24 g of yeast extract, 12 g of tryptone, 0.4% glycerol, and 2.31 g of $KH_2PO_4$ or 12.54 g/L $K_2HPO_4$) to which 50 μg/mL ampicillin had been added, and cultured at 37° C. When the absorbance at 600 nm reached about 3, IPTG with a final concentration of 0.4 mM was added to induce expression of protein. Then, after further culturing for 6 hours, the cells were recovered and the expression was confirmed by SDS-PAGE (FIG. 7).

EXAMPLE 5-2

Isolation and Refolding of Inclusion Body

The cells recovered from the culture were resuspended in TE buffer (50 mM Tris-HCl, 5 mM EDTA, pH 8.0), homogenized using a homogenizer (EmulsiFlex C-3, Avestin), and centrifuged to recover the insoluble inclusion body. By washing 2 times with 1% Triton X-100 and then once with distilled water, the inclusion bodies with the bacteria lysates removed were isolated. In order to obtain IFN and CTP-fused IFN having activity, the isolated inclusion body was dissolved in different optimized solubilization buffers and then refolded by stirring in a refolding buffer. The solubilization and refolding buffers used for each IFN inclusion body and the refolding condition are summarized in Table 3:

TABLE 3

| | Solubilization buffer | Refolding buffer | Refolding condition |
|---|---|---|---|
| IFN | 50 mM glycine, 8M urea, pH 11.0 | 50 mM glycine, 2M urea | pH 9.5; stirring at room temperature for 24 hours |
| N-terminal CTP-fused IFN | 50 mM tris-HCl, 5 mM EDTA, 8M urea, pH 11.0 | 50 mM tris-HCl, 1 mM EDTA, 2M urea, 10% sucrose, 0.1 mM oxidized glutathione and 1 mM reduced glutathione | pH 8; stirring at 4° C. for 4 hours |
| C-terminal CTP-fused IFN | 50 mM tris-HCl, 5 mM EDTA, 8M urea, pH 11.0 | 50 mM tris-HCl, 1 mM EDTA, 2M urea, 0.1 mM oxidized glutathione and 1 mM reduced glutathione | pH 9; stirring at room temperature for 48 hours |

EXAMPLE 5-3

High-Purity Purification by Chromatography

After the refolding, cation exchange chromatography and gel filtration chromatography were carried out to purify the normally refolded IFN or CTP-fused IFN with high purity. Since the isoelectric point of the protein to be isolated is expected at about 6.0 for IFN and at about 9.2 for CTP-fused IFN, the proteins were bound to the CM-Sepharose cation exchanger (Amersham Biosciences) at a lower pH, and fractions were obtained by eluting with the pH and NaCl concentration gradient described in Table 4. The obtained protein fractions were identified by SDS-PAGE. After removing protein multimers from the acquired fractions and concentrating on Centricon with a molecular weight cut-off of 5,000 Da, gel filtration chromatography was carried out to obtain the proteins with high purity.

TABLE 4

| | isoelectric point | Sample binding | Column washing | Elution |
|---|---|---|---|---|
| IFN | ~6.0 | 50 mM acetic acid (pH 4.0) | 50 mM acetic acid (pH 5.5) | 50 mM acetic acid (pH 5.5); NaCl conc. gradient 0-500 mM |
| N-terminal CTP-fused IFN | ~9.2 | 50 mM acetic acid (pH 4.0) | 20 mM tris-HCl (pH 9.0) | 20 mM tris-HCl (pH 9.0); NaCl conc. gradient 0-500 mM |
| C-terminal CTP-fused IFN | ~9.2 | 50 mM acetic acid (pH 4.0) | 20 mM tris-HCl (pH 9.0) | 20 mM tris-HCl (pH 9.0); NaCl conc. gradient 0-1M |

EXAMPLE 6

Measurement of Activity of IFN and CTP-Fused IFN

The IFN and CTP-fused IFN purified in Example 5 were subjected to biological activity test as follows:

EXAMPLE 6-1

Cell Membrane Binding and Residence in Cytoplasm

The purified IFN and CTP-fused IFN were fluorescence-labeled with FITC or rhodamine and then treated to HeLa cells (Korean Cell Line Bank) or HepG2 cells (Korean Cell Line Bank), which had been cultured for 2 days, to a final concentration of 5-10 nM. Then, their distribution was observed using a confocal scanning microscope (LSM 5 Exciter, Carl-Zeiss).

Figure 8:
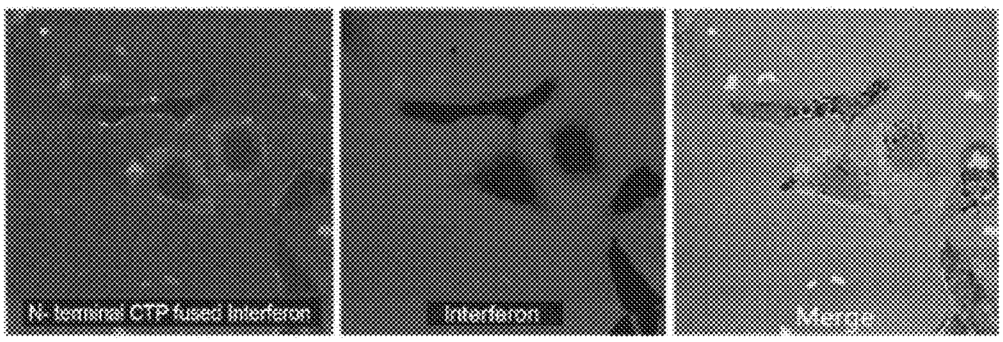
FIG. 8 shows a result of observing the binding of IFN and CTP-IFN proteins to the cell membrane of HeLa cell using a confocal scanning microscope.
Figure 9:
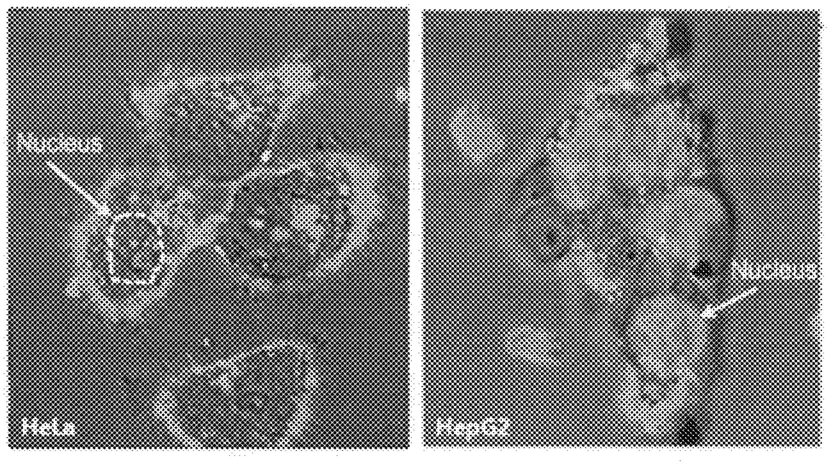
FIG. 9 shows a result of observing using a confocal scanning microscope that the CTP-fused IFN protein remains in the cytoplasm without passing through the nuclear membrane in HeLa or HepG2 cell.

As seen from FIG. 8, CTP-fused IFN showed much stronger binding to the cell membrane than IFN. And, as seen from FIG. 9, the CTP-fused IFN which was translocated into the cell through the cell membrane remained in the cytoplasm without penetrating the nuclear membrane. Thus, it was confirmed that CTP-fused IFN is free from the risk of chromosomal damage in the nucleus by the protein attached thereto.

EXAMPLE 6-2

Translocation into Liver Tissue

① PEGylation of IFN and CTP-Fused IFN

In mice, a protein with a molecular weight smaller than 30 kDa may be quickly excreted by renal clearance, resulting in short residence in the blood making observation of translocation property difficult. To overcome this problem and thus extend residence in blood and make observation of translocation into the liver easier, IFN and CTP-fused IFN, whose molecular weight is about 20 kDa, was PEGylated to increase the molecular weight to at least 40 kDa.

Figure 10:
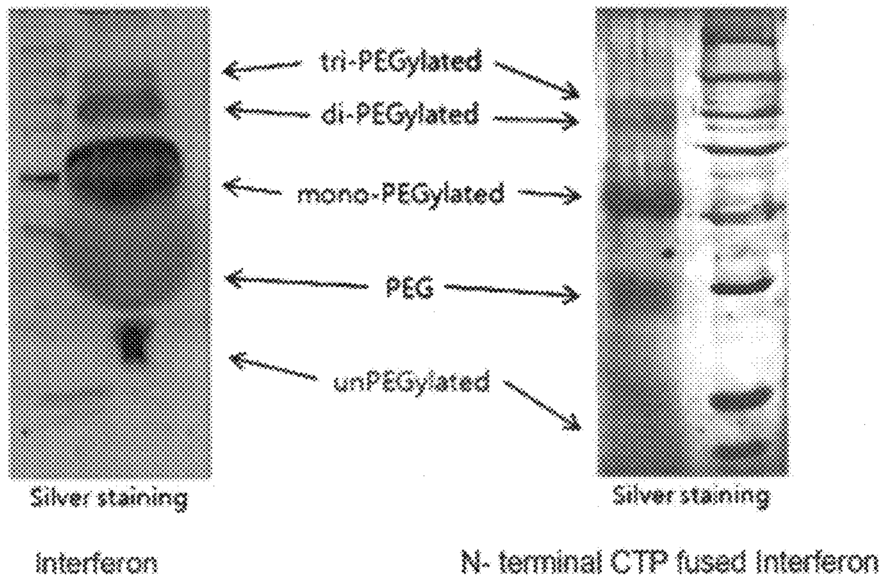
FIG. 10 shows a result of random PEGylation of IFN and CTP-fused IFN proteins.

For this, polyethylene glycol (PEG) NHS ester (Jenkem Biotechnology) with a molecular weight of 20 kDa was used to randomly PEGylate IFN and CTP-fused IFN (FIG. 10). Then, mono-PEGylation IFN and CTP-fused IFN were finally isolated by cation exchange chromatography and gel filtration chromatography.

② Observation of Translocation into Liver Tissue by In Vivo Imaging

The IFN and CTP-fused IFN whose molecular weight was increased to above 40 kDa by PEGylation were fluorescence-labeled with Cy5.5 and administered intravenously to mice at 2 nmol. About 45 minutes later, the distribution of the proteins in the body was observed using IVIS-200 (Xenogen).

Figure 11:
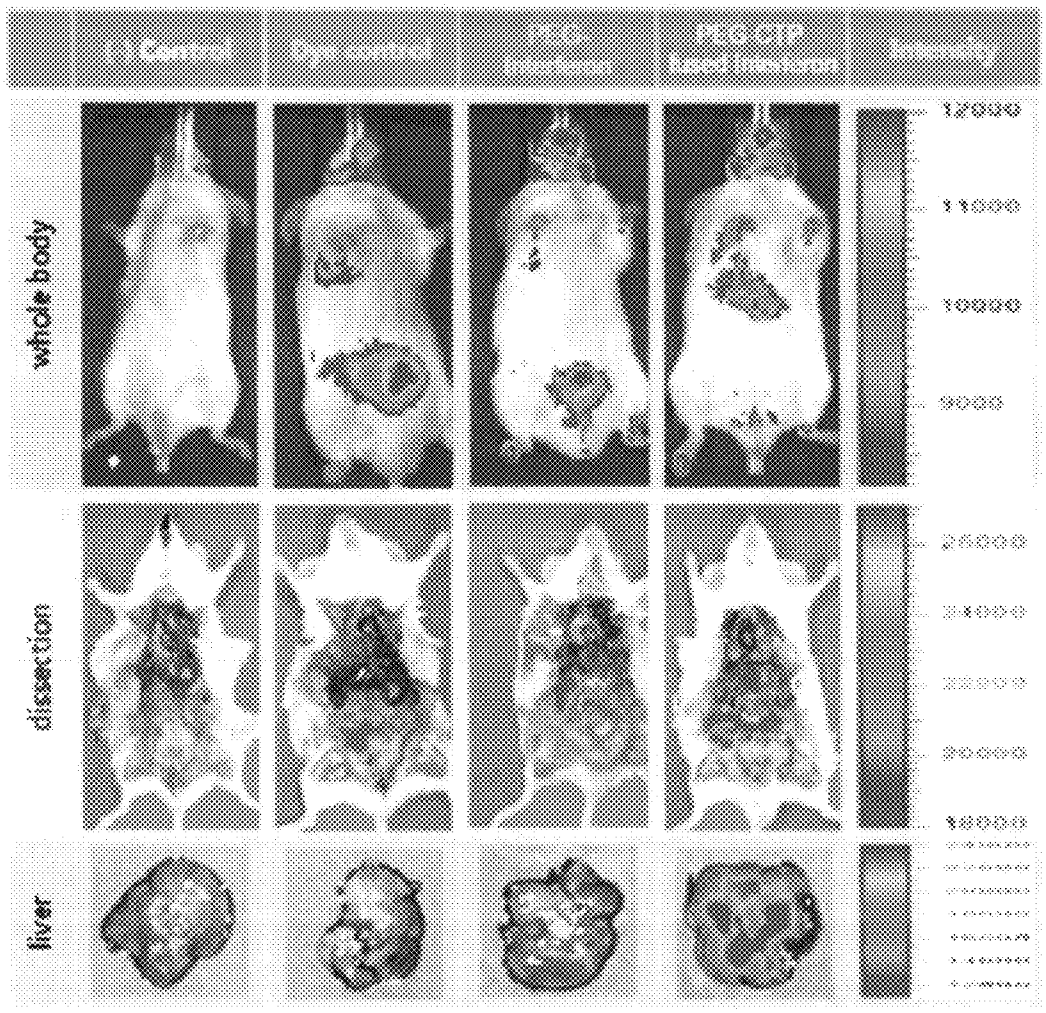
FIG. 11 shows a result of administering PEG-IFN and PEG-CTP fused IFN proteins intravenously to mice and imaging their distribution using the in vivo imaging system IVIS-200.
Figure 12:
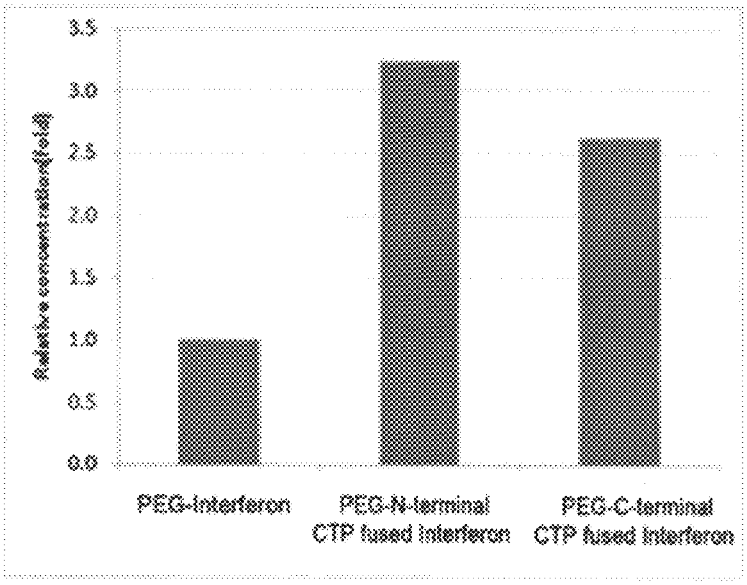
FIG. 12 shows a result of administering PEG-IFN, PEG-N-terminal CTP fused IFN and PEG-C-terminal CTP fused IFN proteins to mice and measuring their relative concentration in the liver tissue.

As seen from FIG. 11, PEG-IFN was excreted to the bladder whereas most of PEG-CTP fused IFN remained in the liver. And, as seen from FIG. 12, when the relative concentration of the proteins in the liver tissue were compared by measuring the fluorescence intensity, the concentration of PEG-N-terminal CTP-fused IFN was about 3.2 fold and that of PEG-C-terminal CTP-fused interferon was about 2.6 fold as compared to PEG-IFN.

Figure 13:
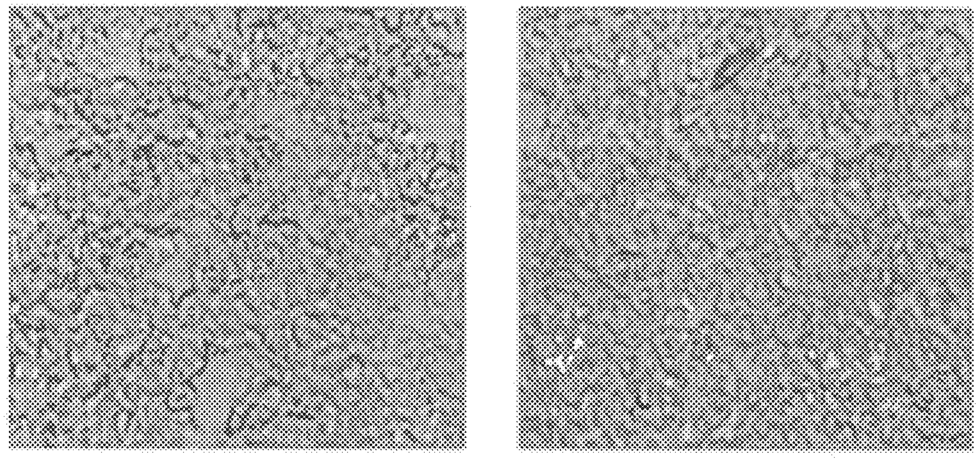
FIG. 13 shows fluorescence microscopic images of mouse liver tissue cryosections obtained after administering PEG-IFN and PEG-CTP fused IFN proteins.

FIG. 13 shows the distribution of the Cy5.5-labeled PEG-IFN and PEG-CTP fused IFN in the mouse liver tissue cryosections observed using a fluorescence microscope. It can be seen that, differently from PEG-IFN, PEG-CTP fused IFN penetrated deep into the liver tissue without remaining on the surface region of the liver.

This suggests that, when a hepatitis treatment is developed using PEG-CTP fused IFN instead of the currently used PEG-IFN, a longer-lasting therapeutic effect can be achieved with less amount of interferon.

③ Measurement of concentration change in liver with time

After fluorescence-labeling and intravenously administering the PEGylation IFN and CTP-fused interferon, the relative concentration of the administered proteins in the liver was determined by measuring the fluorescence intensity.

Figure 14:
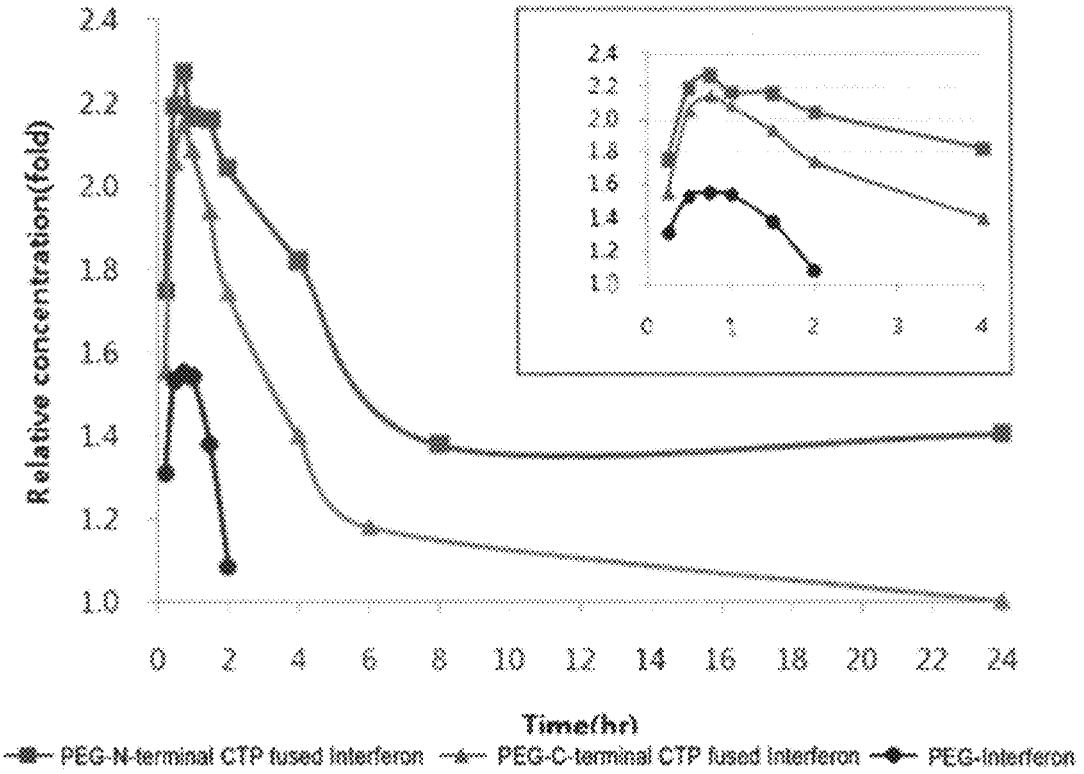
FIG. 14 shows a result of administering PEG-IFN, PEG-N-terminal CTP fused IFN and PEG-C-terminal CTP fused IFN proteins to mice and measuring their relative concentration in the liver tissue with time.

As seen from FIG. 14, the concentration of CTP-fused IFN was highest between 30 and 60 minutes after the administration and decreased slowly thereafter as compared to IFN. Whereas IFN was completely excreted within about 2 hours, the concentration of CTP-fused interferon in the liver was maintained for at least 6 to 24 hours.

This suggests that, when a hepatitis treatment is developed using CTP fused IFN, a longer-lasting therapeutic effect can be achieved with less amount of interferon as compared to the existing interferon drugs.

EXAMPLE 6-3

Measurement of Antiviral Activity

The antiviral activity of purified IFN and CTP-fused IFN was measured by the degree of the cytopathic effect reduced by the proteins in Madin-Darby bovine kidney (MDBK) cells (Korean Cell Line Bank) infected with vesicular stomatitis virus (VSV; Korean Cell Line Bank).

First, MDBK cells were diluted in DMEM medium to $7.5\times10^4$ cells/mL and transferred to a 96-well plate, with 200 μL per each well. After culturing the cells at 37° C. in a 5% $CO_2$ incubator for about 18 hours, IFN and CTP-fused IFN sequentially diluted by 2-fold were treated to induce reaction with interferon. After 4-20 hours, the cells in all the wells were infected with $5\times10^4$ PFU of VSV and further cultured for about 24 hours to induce cytopathic effect. The cultured cells were fixed with formaldehyde, stained with crystal violet, and dried. After dissolving the stain by adding 80% methanol, absorbance was measured at 570 nm.

① Antiviral Activity of Purified Interferon

The antiviral activity of the purified interferon was determined by comparison with known standard interferon. As seen from Table 15, when the antiviral activity was measured after treating with interferon for 20 hours, the purified interferon showed activity comparable (97.7%) to that of the standard. The specific activity was about $2.54\times10^8$ IU/mg, satisfying the international standard ($\geq1.4\times10^8$ IU/mg). In the following activity measurement, the purified interferon, which showed an activity comparable to that of standard, was used as a new standard.

TABLE 5

Antiviral activity of purified interferon

| | Specific activity (IU/mg) | Relative activity | International standard satisfied? |
|---|---|---|---|
| Standard interferon | $2.60\times10^8$ IU/mg | 100% | Yes |
| Purified interferon | $2.54\times10^8$ IU/mg | 97.7% | Yes |

② Antiviral Activity of CTP-Fused IFN, PEG-IFN and PEG-CTP Fused IFN

The antiviral activity of N-terminal CTP-fused IFN, PEG-IFN and PEG-N-terminal CTP fused IFN (FIG. 10) was measured after treating with interferon for 4 hours.

Figure 15:
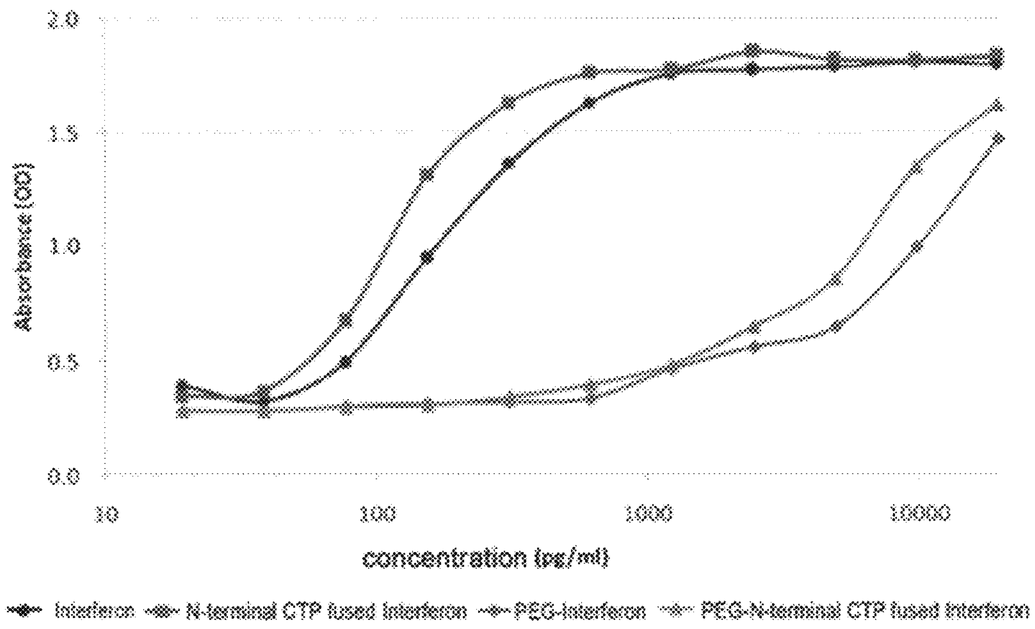
FIG. 15 shows a result of measuring antiviral activity of IFN, PEG-IFN, N-terminal CTP fused IFN and PEG-N-terminal CTP fused IFN proteins.

As seen from FIG. 15, N-terminal CTP-fused IFN showed higher antiviral activity than IFN, and PEG-N-terminal CTP fused IFN showed higher antiviral activity than PEG-IFN. Their specific activity and relative activity are shown in Table 6 and Table 7. It was confirmed that CTP-fused IFN exhibits higher antiviral activity than IFN and that PEG-CTP fused IFN exhibits higher antiviral activity than PEG-IFN.

TABLE 6

Antiviral activity of CTP-fused IFN and IFN

| | Specific activity (IU/mg) | Relative activity (%) |
|---|---|---|
| IFN | $1.75 \times 10^8$ | 100 |
| N-terminal CTP-fused IFN | $2.45 \times 10^8$ | 140 |

TABLE 7

Antiviral activity of PEG-IFN and PEG-CTP fused IFN

| | Specific activity (IU/mg) | Relative activity (%) |
|---|---|---|
| PEG-IFN | $8.93 \times 10^6$ | 100 |
| PEG-N-terminal CTP-fused IFN | $1.30 \times 10^7$ | 145 |

The disclosure provides an IFN-α fused protein wherein a CTP, which binds well to cell-membrane barriers and enables translocation into the liver, is genetically fused to a human IFN-α, thereby enhancing the conjugation capacity of cell membranes and antiviral activity, inhibiting CTP transport into the cell nucleus, and enhancing the translocation and settlement of the fused protein into the liver and of transduction to the liver tissue. Accordingly, it is possible to develop protein-based medicines effective for preventing or treating various liver diseases associated with viral infection at low doses.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

REFERENCES

1. Kwan Sik Lee, Dong Joon Kim et al. Management of Chronic Hepatitis B, *The Korean Journal of Hepatology.;* 13: 447-488 (2007).

2. M. Robinson, R. Lilley, S. Little et al. Codon usage can affect efficiency of translation of genes in *Escherichia coli, Nucleic Acids Res.;* 12: 6663-671 (1984).

3. I. G. Ivanov, R. Alexandrova, B. Dragulev et al. Effect of tandemly repeated AGG triplets on the translation of CAT-mRNA in *E. coli, FEBS Lett.;* 307: 173-176 (1992).

4. I. G. Ivanov, N. Markova et al. Constitutive expression of native human interferon-α gene in *E. coli, Int. J. Biochem.;* 21: 983-985 (1989).

5. R. Alexandrova, M. Eweida et al. Domains in human interferon-alpha 1 gene containing tandems of arginine codons AGG play the role of translational initiators in *E. coli, Int. J. Biochem. Cell Biol.;* 27: 469-473 (1995).

6. R. M. Horton, Z. Cai et al. Gene splicing by overlap extension: tailor-made genes using the polymerase chain reaction, *Biotechniques;* 8: 528-535 (1990).

The invention claimed is:

1. A fusion protein comprising interferon-α (IFN-α) protein fused to a cytoplasmic transduction peptide (CTP), wherein the fusion protein comprises the amino acid sequence of SEQ ID NO: 30 and further comprises polyethylene glycol (PEG) bound thereto.

2. The fusion protein according to claim 1, wherein the PEG has a molecular weight of 10-100 kDa.

3. A nucleotide molecule coding for a fusion protein comprising interferon-α (IFN-α) protein fused to a cytoplasmic transduction peptide (CTP), wherein the fusion protein comprises the amino acid sequence of SEQ ID NO: 30.

4. A vector comprising the nucleotide molecule according to claim 3.

5. An isolated transformant comprising the vector according to claim 4.

6. A method for preparing a fusion protein comprising interferon-α (IFN-α) protein fused to a cytoplasmic transduction peptide (CTP), comprising:

preparing an expression vector comprising the nucleotide molecule according to claim 3 operably linked to a promoter;

culturing a transformant transformed with the expression vector; and obtaining the fusion protein from the cultured transformant.

7. A method for purifying a fusion protein comprising interferon-α (IFN-α) protein fused to a cytoplasmic transduction peptide (CTP), comprising:

culturing a transformant transformed with an expression vector comprising the nucleotide molecule according to claim 3 operably linked to a promoter;

obtaining an inclusion body comprising the fusion protein from the cultured transformant; and lysing the inclusion body in a solubilization buffer of pH 10-12 and stirring the resultant at 4-25° C. and pH 8-10 in a refolding buffer.

8. The method according to claim 7, wherein the solubilization buffer comprises tris-HCl, EDTA and urea, and the refolding buffer is selected from the group consisting of tris-HCl, EDTA, urea, sucrose, and oxidized or reduced glutathione.

9. A pharmaceutical composition for treating a liver disease comprising: a pharmaceutically effective amount of the fusion protein according to claim 1; and a pharmaceutically acceptable carrier, wherein the liver disease is liver cancer or hepatitis.

10. The pharmaceutical composition according to claim 9, wherein the composition is formulated for intravascular administration.

11. A method for treating a liver disease, comprising administering a pharmaceutical composition comprising: a pharmaceutically effective amount of the IFN-αfused protein according to claim 1; and a pharmaceutically acceptable carrier to a subject, wherein the liver disease is liver cancer or hepatitis.

12. The method composition according to claim 11, wherein the composition is administered intravascularly.

13. A fusion protein comprising IFN-α fused to a cytoplasmic transduction peptide (CTP), wherein the CTP is fused at the C-terminus of the IFN-α, and wherein the fused protein comprises the amino acid sequence of SEQ ID NO: 32.

14. A nucleotide molecule coding for a fusion protein comprising IFN-α protein fused to a cytoplasmic transduction peptide (CTP), wherein the fusion protein comprises the amino acid sequence of SEQ ID NO: 32.

15. A vector comprising the nucleotide molecule according to claim 14.

16. An isolated transformant comprising the vector according to claim 15.

17. A method for preparing a fused protein comprising IFN-α protein fused to a cytoplasmic transduction peptide (CTP), comprising:

preparing an expression vector comprising the nucleotide molecule according to claim 14 operably linked to a promoter;

culturing a transformant transformed with the expression vector; and obtaining the fusion protein from the cultured transformant.

18. A method for purifying a fusion protein comprising IFN-α protein fused to a cytoplasmic transduction peptide (CTP), comprising:

culturing a transformant transformed with an expression vector comprising the nucleotide molecule according to claim 14 operably linked to a promoter;

obtaining an inclusion body comprising the fusion protein from the cultured transformant; and lysing the inclusion body in a solubilization buffer of pH 10-12 and stirring the resultant at 4-25° C. and pH 8-10 in a refolding buffer.

19. The method according to claim 18, wherein the solubilization buffer comprises tris-HCl, EDTA, and urea, and the refolding buffer is selected from the group consisting of tris-HCl, EDTA, urea, sucrose, and oxidized or reduced glutathione.

20. A pharmaceutical composition for treating a liver disease comprising:

a pharmaceutically effective amount of the fusion protein according to claim 13; and a pharmaceutically acceptable carrier;

wherein the liver disease is liver cancer or hepatitis.

21. The pharmaceutical composition according to claim 20, wherein the composition is formulated for intravascular administration.

22. A method for treating a liver disease, comprising administering a pharmaceutical composition comprising: a pharmaceutically effective amount of the IFN-α fused protein according to claim 13; and a pharmaceutically acceptable carrier to a subject, wherein the liver disease is liver cancer or hepatitis.

23. The method according to claim 22, wherein the composition is administered intravascularly.

* * * * *

```
                    SEQUENCE LISTING


<160> NUMBER OF SEQ ID NOS: 32

<210> SEQ ID NO 1
<211> LENGTH: 99
<212> TYPE: DNA
<213> ORGANISM: Artificial Sequence
<220> FEATURE:
<223> OTHER INFORMATION: a oligomer sequence for obtaining human
      IFN-alpha2b gene

<400> SEQUENCE: 1

tgcgatctgc cgcagaccca tagcctgggc agccgtcgta ccctgatgct gctggcgcag     60

atgcgtcgta tcagcctgtt tagctgcctg aaagatcgt                            99


<210> SEQ ID NO 2
<211> LENGTH: 99
<212> TYPE: DNA
<213> ORGANISM: Artificial Sequence
<220> FEATURE:
<223> OTHER INFORMATION: (sIFN-2)a oligomer sequence for obtaining human
      IFN-alpha2b gene

<400> SEQUENCE: 2

gatcatttca tgcagcaccg ggatggtttc cgctttctga aactggttgc caaattcttc     60

ctgcggaaag ccaaaatcat gacgatcttt caggcagct                            99


<210> SEQ ID NO 3
<211> LENGTH: 99
<212> TYPE: DNA
<213> ORGANISM: Artificial Sequence
<220> FEATURE:
<223> OTHER INFORMATION: (sIFN-3)a oligomer sequence for obtaining human
```

IFN-alpha2b gene

<400> SEQUENCE: 3
gtgctgcatg aaatgatcca gcagatcttt aacctgttta gcaccaaaga tagcagcgcg 60
gcgtgggatg aaaccctgct ggataaattt tataccgaa 99

<210> SEQ ID NO 4
<211> LENGTH: 99
<212> TYPE: DNA
<213> ORGANISM: Artificial Sequence
<220> FEATURE:
<223> OTHER INFORMATION: (sIFN-4)a oligomer sequence for obtaining human IFN-alpha2b gene

<400> SEQUENCE: 4
atcttctttc atcagcgggg tttcggtcac gcccacgccc tggatcacgc acgcttccag 60
atcgttcagc tgctgataca gttcggtata aaatttatc 99

<210> SEQ ID NO 5
<211> LENGTH: 99
<212> TYPE: DNA
<213> ORGANISM: Artificial Sequence
<220> FEATURE:
<223> OTHER INFORMATION: (sIFN-5)a oligomer sequence for obtaining human IFN-alpha2b gene

<400> SEQUENCE: 5
ccgctgatga aagaagatag catcctggcg gtgcgtaaat attttcagcg tatcaccctg 60
tatctgaaag aaaaaaaata tagcccgtgc gcgtgggaa 99

<210> SEQ ID NO 6
<211> LENGTH: 96
<212> TYPE: DNA
<213> ORGANISM: Artificial Sequence
<220> FEATURE:
<223> OTHER INFORMATION: (sIFN-6)a oligomer sequence for obtaining human IFN-alpha2b gene

<400> SEQUENCE: 6
ctattattct ttgctacgca ggctttcttg caggttggtg ctcaggctaa agctacgcat 60
gatttccgca cgcaccactt cccacgcgca cgggct 96

<210> SEQ ID NO 7
<211> LENGTH: 51
<212> TYPE: DNA
<213> ORGANISM: Artificial Sequence
<220> FEATURE:
<223> OTHER INFORMATION: (CFN-1)a primer sequence for obtaining IFN-alpha fusion protein fused to CTP

<400> SEQUENCE: 7
tatggtcgtc gtgcacgtcg tcgtcgtcgt cgttgcgatc tgccgcagac c 51

<210> SEQ ID NO 8
<211> LENGTH: 53
<212> TYPE: DNA
<213> ORGANISM: Artificial Sequence
<220> FEATURE:
<223> OTHER INFORMATION: (CFN-2)a primer sequence for obtaining IFN-alpha fusion protein fused to CTP

<400> SEQUENCE: 8
taatctagaa aaaaccaagg aggtaataac atatgtatgg tcgtcgtgca cgt 53

-continued

<210> SEQ ID NO 9
<211> LENGTH: 39
<212> TYPE: DNA
<213> ORGANISM: Artificial Sequence
<220> FEATURE:
<223> OTHER INFORMATION: (CFN-3)a primer sequence for obtaining
IFN-alpha fusion protein fused to CTP

<400> SEQUENCE: 9
caaggatccc tcgagctatt attctttgct acgcaggct 39

<210> SEQ ID NO 10
<211> LENGTH: 50
<212> TYPE: DNA
<213> ORGANISM: Artificial Sequence
<220> FEATURE:
<223> OTHER INFORMATION: (CFN-4)a primer sequence for obtaining
IFN-alpha fusion protein fused to CTP

<400> SEQUENCE: 10
gcctctagaa aaaaccaagg aggtaataac atatgtgcga tctgccgcag 50

<210> SEQ ID NO 11
<211> LENGTH: 45
<212> TYPE: DNA
<213> ORGANISM: Artificial Sequence
<220> FEATURE:
<223> OTHER INFORMATION: (CFN-5)a primer sequence for obtaining
IFN-alpha fusion protein fused to CTP

<400> SEQUENCE: 11
acgacgacga cgtgcacgac gaccatattc tttgctacgc aggct 45

<210> SEQ ID NO 12
<211> LENGTH: 45
<212> TYPE: DNA
<213> ORGANISM: Artificial Sequence
<220> FEATURE:
<223> OTHER INFORMATION: (CFN-6)a primer sequence for obtaining
IFN-alpha fusion protein fused to CTP

<400> SEQUENCE: 12
taaggatccc tcgagctatt aacgacgacg acgacgacgt gcacg 45

<210> SEQ ID NO 13
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 13

Tyr Gly Arg Arg Ala Arg Arg Arg Arg Arg Arg
1 5 10

<210> SEQ ID NO 14
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 14

Tyr Gly Arg Arg Ala Arg Arg Arg Ala Arg Arg
1 5 10

<210> SEQ ID NO 15
<211> LENGTH: 11

-continued

<212> TYPE: PRT
<213> ORGANISM: Artificial Sequence
<220> FEATURE:
<223> OTHER INFORMATION: cytoplasmic transduction peptide

<400> SEQUENCE: 15

Tyr Gly Arg Arg Ala Arg Arg Ala Ala Arg Arg
1 5 10

<210> SEQ ID NO 16
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 16

Tyr Lys Arg Lys Ala Arg Arg Ala Ala Arg Arg
1 5 10

<210> SEQ ID NO 17
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 17

Tyr Ala Arg Lys Ala Arg Arg Ala Ala Arg Arg
1 5 10

<210> SEQ ID NO 18
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 18

Tyr Lys Arg Ala Ala Arg Arg Ala Ala Arg Arg
1 5 10

<210> SEQ ID NO 19
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 19

Tyr Glu Arg Glu Ala Arg Arg Ala Ala Arg Arg
1 5 10

<210> SEQ ID NO 20
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 20

Tyr Ala Arg Glu Ala Arg Arg Ala Ala Arg Arg
1 5 10

<210> SEQ ID NO 21
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 21

Tyr Gly Arg Ala Ala Arg Arg Ala Ala Arg Arg
1 5 10

<210> SEQ ID NO 22
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 22

Tyr Arg Arg Ala Ala Arg Arg Ala Ala Arg Ala
1 5 10

<210> SEQ ID NO 23
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 23

Tyr Pro Arg Ala Ala Arg Arg Ala Ala Arg Arg
1 5 10

<210> SEQ ID NO 24
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 24

Pro Ala Arg Ala Ala Arg Arg Ala Ala Arg Arg
1 5 10

<210> SEQ ID NO 25
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 25

Tyr Gly Arg Arg Arg Arg Arg Arg Arg Arg Arg
1 5 10

<210> SEQ ID NO 26
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 26

Tyr Arg Arg Arg Arg Arg Arg Arg Arg Arg Arg
1 5 10

<210> SEQ ID NO 27
<211> LENGTH: 545
<212> TYPE: DNA
<213> ORGANISM: Artificial Sequence
<220> FEATURE:
<223> OTHER INFORMATION: (sIFN)PCR synthesis gene of human IFN-alpha

<220> FEATURE:
<221> NAME/KEY: CDS
<222> LOCATION: (30)..(527)

<400> SEQUENCE: 27
tctagaaaaa accaaggagg taataacat atg tgc gat ctg ccg cag acc cat 53
Met Cys Asp Leu Pro Gln Thr His
1 5 agc ctg ggc agc cgt cgt acc ctg atg ctg ctg gcg cag atg cgt cgt 101
Ser Leu Gly Ser Arg Arg Thr Leu Met Leu Leu Ala Gln Met Arg Arg
10 15 20 atc agc ctg ttt agc tgc ctg aaa gat cgt cat gat ttt ggc ttt ccg 149
Ile Ser Leu Phe Ser Cys Leu Lys Asp Arg His Asp Phe Gly Phe Pro
25 30 35 40 cag gaa gaa ttt ggc aac cag ttt cag aaa gcg gaa acc atc ccg gtg 197
Gln Glu Glu Phe Gly Asn Gln Phe Gln Lys Ala Glu Thr Ile Pro Val
45 50 55 ctg cat gaa atg atc cag cag atc ttt aac ctg ttt agc acc aaa gat 245
Leu His Glu Met Ile Gln Gln Ile Phe Asn Leu Phe Ser Thr Lys Asp
60 65 70 agc agc gcg gcg tgg gat gaa acc ctg ctg gat aaa ttt tat acc gaa 293
Ser Ser Ala Ala Trp Asp Glu Thr Leu Leu Asp Lys Phe Tyr Thr Glu
75 80 85 ctg tat cag cag ctg aac gat ctg gaa gcg tgc gtg atc cag ggc gtg 341
Leu Tyr Gln Gln Leu Asn Asp Leu Glu Ala Cys Val Ile Gln Gly Val
90 95 100 ggc gtg acc gaa acc ccg ctg atg aaa gaa gat agc atc ctg gcg gtg 389
Gly Val Thr Glu Thr Pro Leu Met Lys Glu Asp Ser Ile Leu Ala Val
105 110 115 120 cgt aaa tat ttt cag cgt atc acc ctg tat ctg aaa gaa aaa aaa tat 437
Arg Lys Tyr Phe Gln Arg Ile Thr Leu Tyr Leu Lys Glu Lys Lys Tyr
125 130 135 agc ccg tgc gcg tgg gaa gtg gtg cgt gcg gaa atc atg cgt agc ttt 485
Ser Pro Cys Ala Trp Glu Val Val Arg Ala Glu Ile Met Arg Ser Phe
140 145 150 agc ctg agc acc aac ctg caa gaa agc ctg cgt agc aaa gaa 527
Ser Leu Ser Thr Asn Leu Gln Glu Ser Leu Arg Ser Lys Glu
155 160 165 taatagctcg agggatcc 545

<210> SEQ ID NO 28
<211> LENGTH: 166
<212> TYPE: PRT
<213> ORGANISM: Artificial Sequence
<220> FEATURE:
<223> OTHER INFORMATION: Synthetic Construct

<400> SEQUENCE: 28

Met Cys Asp Leu Pro Gln Thr His Ser Leu Gly Ser Arg Arg Thr Leu
1 5 10 15

Met Leu Leu Ala Gln Met Arg Arg Ile Ser Leu Phe Ser Cys Leu Lys
20 25 30

Asp Arg His Asp Phe Gly Phe Pro Gln Glu Glu Phe Gly Asn Gln Phe
35 40 45

Gln Lys Ala Glu Thr Ile Pro Val Leu His Glu Met Ile Gln Gln Ile
50 55 60

Phe Asn Leu Phe Ser Thr Lys Asp Ser Ser Ala Ala Trp Asp Glu Thr
65 70 75 80

Leu Leu Asp Lys Phe Tyr Thr Glu Leu Tyr Gln Gln Leu Asn Asp Leu
85 90 95

-continued

```
Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165


<210> SEQ ID NO 29
<211> LENGTH: 578
<212> TYPE: DNA
<213> ORGANISM: Artificial Sequence
<220> FEATURE:
<223> OTHER INFORMATION: (CTP-sIFN)PCR synthesis gene fused CTP to
      N-terminal of human IFN-alpha
<220> FEATURE:
<221> NAME/KEY: CDS
<222> LOCATION: (30)..(560)

<400> SEQUENCE: 29

tctagaaaaa accaaggagg taataacat atg tat ggt cgt cgt gca cgt cgt       53
                                Met Tyr Gly Arg Arg Ala Arg Arg
                                1               5

cgt cgt cgt cgt tgc gat ctg ccg cag acc cat agc ctg ggc agc cgt      101
Arg Arg Arg Arg Cys Asp Leu Pro Gln Thr His Ser Leu Gly Ser Arg
    10                  15                  20

cgt acc ctg atg ctg ctg gcg cag atg cgt cgt atc agc ctg ttt agc      149
Arg Thr Leu Met Leu Leu Ala Gln Met Arg Arg Ile Ser Leu Phe Ser
25                  30                  35                  40

tgc ctg aaa gat cgt cat gat ttt ggc ttt ccg cag gaa gaa ttt ggc      197
Cys Leu Lys Asp Arg His Asp Phe Gly Phe Pro Gln Glu Glu Phe Gly
                45                  50                  55

aac cag ttt cag aaa gcg gaa acc atc ccg gtg ctg cat gaa atg atc      245
Asn Gln Phe Gln Lys Ala Glu Thr Ile Pro Val Leu His Glu Met Ile
            60                  65                  70

cag cag atc ttt aac ctg ttt agc acc aaa gat agc agc gcg gcg tgg      293
Gln Gln Ile Phe Asn Leu Phe Ser Thr Lys Asp Ser Ser Ala Ala Trp
        75                  80                  85

gat gaa acc ctg ctg gat aaa ttt tat acc gaa ctg tat cag cag ctg      341
Asp Glu Thr Leu Leu Asp Lys Phe Tyr Thr Glu Leu Tyr Gln Gln Leu
    90                  95                  100

aac gat ctg gaa gcg tgc gtg atc cag ggc gtg ggc gtg acc gaa acc      389
Asn Asp Leu Glu Ala Cys Val Ile Gln Gly Val Gly Val Thr Glu Thr
105                 110                 115                 120

ccg ctg atg aaa gaa gat agc atc ctg gcg gtg cgt aaa tat ttt cag      437
Pro Leu Met Lys Glu Asp Ser Ile Leu Ala Val Arg Lys Tyr Phe Gln
                125                 130                 135

cgt atc acc ctg tat ctg aag gaa aaa aaa tat agc ccg tgc gcg tgg      485
Arg Ile Thr Leu Tyr Leu Lys Glu Lys Lys Tyr Ser Pro Cys Ala Trp
            140                 145                 150

gaa gtg gtg cgt gcg gaa atc atg cgt agc ttt agc ctg agc acc aac      533
Glu Val Val Arg Ala Glu Ile Met Arg Ser Phe Ser Leu Ser Thr Asn
        155                 160                 165

ctg caa gaa agc ctg cgt agc aaa gaa taatagctcg agggatcc              578
Leu Gln Glu Ser Leu Arg Ser Lys Glu
    170                 175


<210> SEQ ID NO 30
<211> LENGTH: 177
```

```
<212> TYPE: PRT
<213> ORGANISM: Artificial Sequence
<220> FEATURE:
<223> OTHER INFORMATION: Synthetic Construct

<400> SEQUENCE: 30

Met Tyr Gly Arg Arg Ala Arg Arg Arg Arg Arg Arg Cys Asp Leu Pro
1               5                   10                  15

Gln Thr His Ser Leu Gly Ser Arg Arg Thr Leu Met Leu Leu Ala Gln
            20                  25                  30

Met Arg Arg Ile Ser Leu Phe Ser Cys Leu Lys Asp Arg His Asp Phe
        35                  40                  45

Gly Phe Pro Gln Glu Glu Phe Gly Asn Gln Phe Gln Lys Ala Glu Thr
    50                  55                  60

Ile Pro Val Leu His Glu Met Ile Gln Gln Ile Phe Asn Leu Phe Ser
65                  70                  75                  80

Thr Lys Asp Ser Ser Ala Ala Trp Asp Glu Thr Leu Leu Asp Lys Phe
                85                  90                  95

Tyr Thr Glu Leu Tyr Gln Gln Leu Asn Asp Leu Glu Ala Cys Val Ile
            100                 105                 110

Gln Gly Val Gly Val Thr Glu Thr Pro Leu Met Lys Glu Asp Ser Ile
        115                 120                 125

Leu Ala Val Arg Lys Tyr Phe Gln Arg Ile Thr Leu Tyr Leu Lys Glu
    130                 135                 140

Lys Lys Tyr Ser Pro Cys Ala Trp Glu Val Val Arg Ala Glu Ile Met
145                 150                 155                 160

Arg Ser Phe Ser Leu Ser Thr Asn Leu Gln Glu Ser Leu Arg Ser Lys
                165                 170                 175

Glu


<210> SEQ ID NO 31
<211> LENGTH: 579
<212> TYPE: DNA
<213> ORGANISM: Artificial Sequence
<220> FEATURE:
<223> OTHER INFORMATION: (sIFN-CTP)PCR synthesis gene fused CTP to
      C-terminal of human IFN-alpha
<220> FEATURE:
<221> NAME/KEY: CDS
<222> LOCATION: (31)..(561)

<400> SEQUENCE: 31

tctagaaaaa accaaggagg taataaacat atg tgc gat ctg ccg cag acc cat      54
                                 Met Cys Asp Leu Pro Gln Thr His
                                 1               5

agc ctg ggc agc cgt cgt acc ctg atg ctg ctg gcg cag atg cgt cgt      102
Ser Leu Gly Ser Arg Arg Thr Leu Met Leu Leu Ala Gln Met Arg Arg
    10                  15                  20

atc agc ctg ttt agc tgc ctg aaa gat cgt cat gat ttt ggc ttt ccg      150
Ile Ser Leu Phe Ser Cys Leu Lys Asp Arg His Asp Phe Gly Phe Pro
25                  30                  35                  40

cag gaa gaa ttt ggc aac cag ttt cag aaa gcg gaa acc atc ccg gtg      198
Gln Glu Glu Phe Gly Asn Gln Phe Gln Lys Ala Glu Thr Ile Pro Val
                45                  50                  55

ctg cat gaa atg atc cag cag atc ttt aac ctg ttt agc acc aaa gat      246
Leu His Glu Met Ile Gln Gln Ile Phe Asn Leu Phe Ser Thr Lys Asp
            60                  65                  70

agc agc gcg gcg tgg gat gaa acc ctg ctg gat aaa ttt tat acc gaa      294
Ser Ser Ala Ala Trp Asp Glu Thr Leu Leu Asp Lys Phe Tyr Thr Glu
        75                  80                  85
```

-continued

```
ctg tat cag cag ctg aac gat ctg gaa gcg tgc gtg atc cag ggc gtg      342
Leu Tyr Gln Gln Leu Asn Asp Leu Glu Ala Cys Val Ile Gln Gly Val
    90                  95                  100

ggc gtg acc gaa acc ccg ctg atg aaa gaa gat agc atc ctg gcg gtg      390
Gly Val Thr Glu Thr Pro Leu Met Lys Glu Asp Ser Ile Leu Ala Val
105                 110                 115                 120

cgt aaa tat ttt cag cgt atc acc ctg tat ctg aaa gaa aaa aaa tat      438
Arg Lys Tyr Phe Gln Arg Ile Thr Leu Tyr Leu Lys Glu Lys Lys Tyr
                125                 130                 135

agc ccg tgc gcg tgg gaa gtg gtg cgt gcg gaa atc atg cgt agc ttt      486
Ser Pro Cys Ala Trp Glu Val Val Arg Ala Glu Ile Met Arg Ser Phe
            140                 145                 150

agc ctg agc acc aac ctg caa gaa agc ctg cgt agc aaa gaa tat ggt      534
Ser Leu Ser Thr Asn Leu Gln Glu Ser Leu Arg Ser Lys Glu Tyr Gly
        155                 160                 165

cgt cgt gca cgt cgt cgt cgt cgt cgt taatagctcg agggatcc              579
Arg Arg Ala Arg Arg Arg Arg Arg Arg
    170                 175


<210> SEQ ID NO 32
<211> LENGTH: 177
<212> TYPE: PRT
<213> ORGANISM: Artificial Sequence
<220> FEATURE:
<223> OTHER INFORMATION: Synthetic Construct

<400> SEQUENCE: 32

Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Tyr Gly Arg Arg Ala Arg Arg Arg Arg Arg
                165                 170                 175

Arg
```